(12) United States Patent
Hsieh et al.

(10) Patent No.: US 9,384,942 B2
(45) Date of Patent: Jul. 5, 2016

(54) SPECIMEN PREPARATION FOR TRANSMISSION ELECTRON MICROSCOPY

(71) Applicants: NATIONAL HEALTH RESEARCH INSTITUTES, Zhunan Town (TW); MATERIALS ANALYSIS TECHNOLOGY (US) CORP, San Jose, CA (US)

(72) Inventors: Yong-fen Hsieh, Hsinchu (TW); Chih-hsun Chu, Hsinchu (TW); Pradeep Sharma, Hsinchu (TW); Yu-feng Ko, Hsinchu (TW); Chung-shi Yang, Zhunan (TW); Lin-ai Tai, Zhunan (TW); Yu-ching Chen, Zhunan (TW); Hsiao-chun Ting, Zhunan (TW)

(73) Assignees: NATIONAL HEALTH RESEARCH INSTITUTES, Miaoli County (TW); MATERIALS ANALYSIS TECHNOLOGY (US) CORP., San Jose, CA (US)

(*) Notice: Subject to any disclaimer, the term of this patent is extended or adjusted under 35 U.S.C. 154(b) by 0 days.

(21) Appl. No.: 14/412,653

(22) PCT Filed: Jul. 8, 2013

(86) PCT No.: PCT/US2013/049595
§ 371 (c)(1),
(2) Date: Jan. 2, 2015

(87) PCT Pub. No.: WO2014/011563
PCT Pub. Date: Jan. 16, 2014

(65) Prior Publication Data
US 2015/0194288 A1    Jul. 9, 2015

(51) Int. Cl.
*H01J 37/00*    (2006.01)
*H01J 37/26*    (2006.01)
(Continued)

(52) U.S. Cl.
CPC .............. *H01J 37/261* (2013.01); *B01L 3/508* (2013.01); *G01N 1/28* (2013.01); *G01N 1/4022* (2013.01);
(Continued)

(58) Field of Classification Search
CPC ......... H01J 37/261; H01J 37/20; H01J 37/16; H01J 37/222; H01J 2237/2007; H01J 2237/2602; H01J 2237/2802; G01N 1/28; G01N 23/02; G01N 1/4022; G01N 2001/4027; B01L 3/508; B01L 2200/0678
USPC ..................... 250/306, 307, 310, 311, 440.11
See application file for complete search history.

(56) References Cited

U.S. PATENT DOCUMENTS 7,807,979 B2 * 10/2010 Liu ..................... H01J 37/20
                                                    250/306
2013/0264476 A1 * 10/2013 Damiano, Jr. ........... H01J 37/20
                                                    250/307

OTHER PUBLICATIONS

Tai, Lin-Ai et al. (2012) "Quantitative Characterization of Nanoparticles in Blood by Transmission Electron Microscopy with a Window-Type Microchip Nanopipet" Anal. Chem. 84, 6312-6316.

*Primary Examiner* — Michael Maskell
(74) *Attorney, Agent, or Firm* — Hsiu-Ming Saunders; Intellectual Property Connections, Inc.

(57) ABSTRACT

A TEM specimen kit is disclosed, which comprises: (a) a top substrate and a bottom substrate, the top and the bottom substrates being transparent and substantially parallel to each other; (b) a first spacer and a second spacer, located beneath the top substrate and sitting on the bottom substrate, the second spacer being opposite to and spaced apart from the first spacer at a distance of d; and (c) a chamber formed between the top and bottom substrate and between the first and second spacer, the chamber having two ends open to the atmosphere and characterized by having a height defined by the thickness h of the spacer, wherein the height being smaller than the diameter of a red blood cell. Also enclosed are methods for preparing a dry specimen for TEM nanoparticle characterization, and methods for analyzing TEM images of nanoparticles in a liquid sample.

15 Claims, 8 Drawing Sheets

(51) Int. Cl.
*B01L 3/00* (2006.01)
*G01N 1/40* (2006.01)
*G01N 23/02* (2006.01)
*G01N 1/28* (2006.01)
*H01J 37/16* (2006.01)
*H01J 37/22* (2006.01)
*H01J 37/20* (2006.01)

(52) U.S. Cl.
CPC .............. *G01N 23/02* (2013.01); *H01J 37/16* (2013.01); *H01J 37/20* (2013.01); *H01J 37/222* (2013.01); *B01L 2200/0678* (2013.01); *B01L 2300/0822* (2013.01); *G01N 2001/4027* (2013.01); *H01J 2237/2007* (2013.01); *H01J 2237/2602* (2013.01); *H01J 2237/2802* (2013.01)

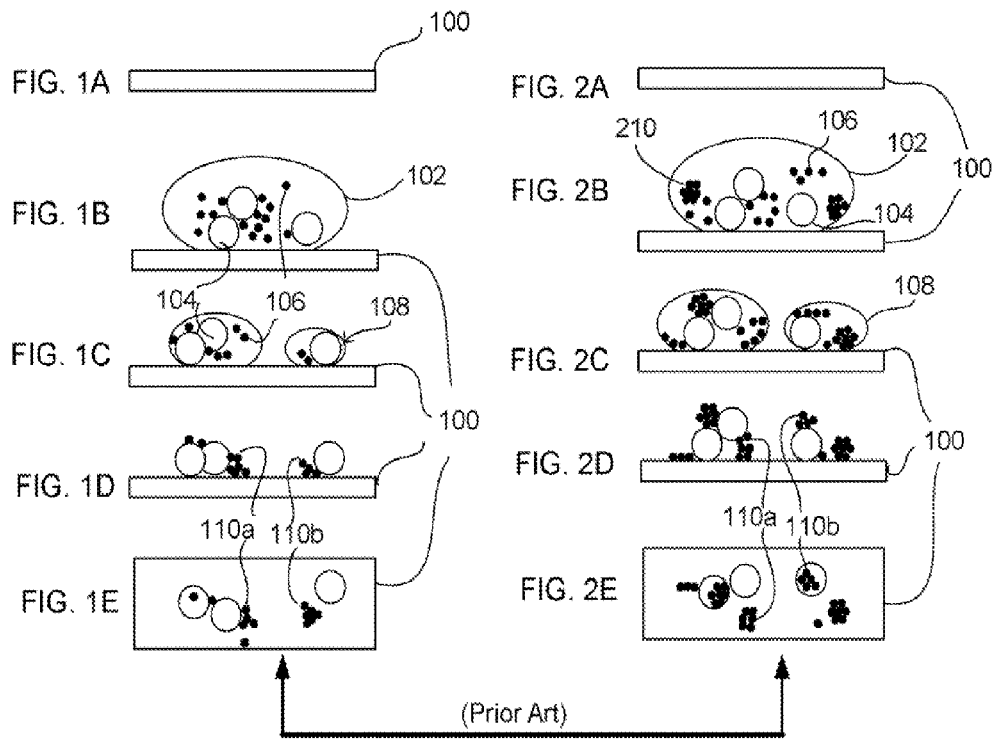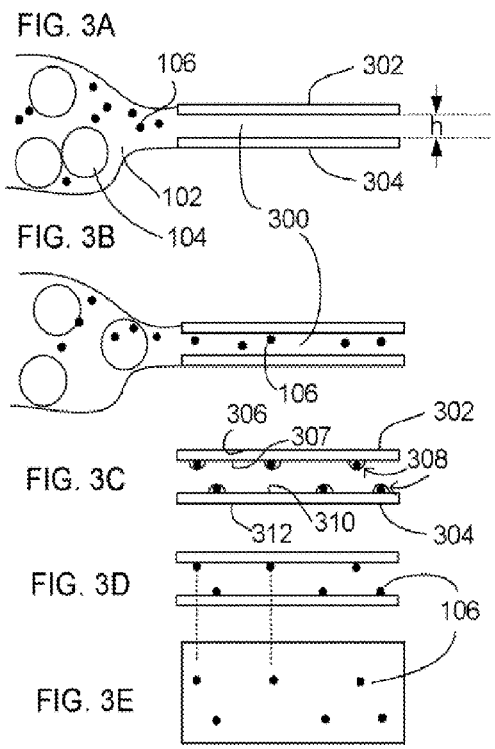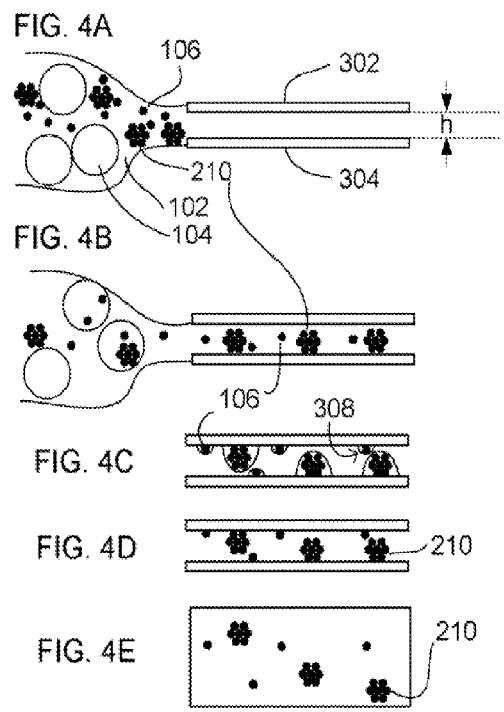

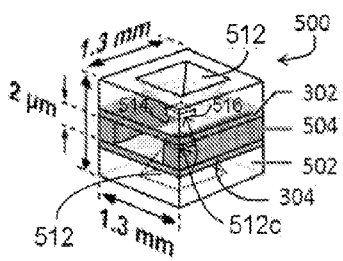
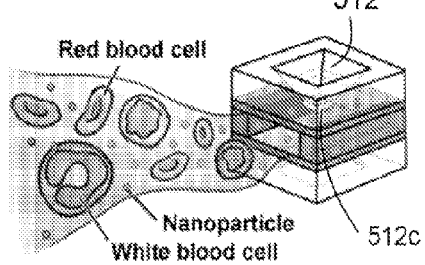
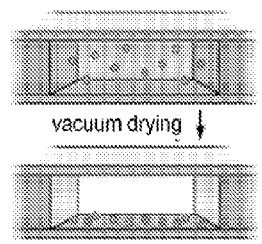
FIG. 10A  FIG. 10B  FIG. 10C
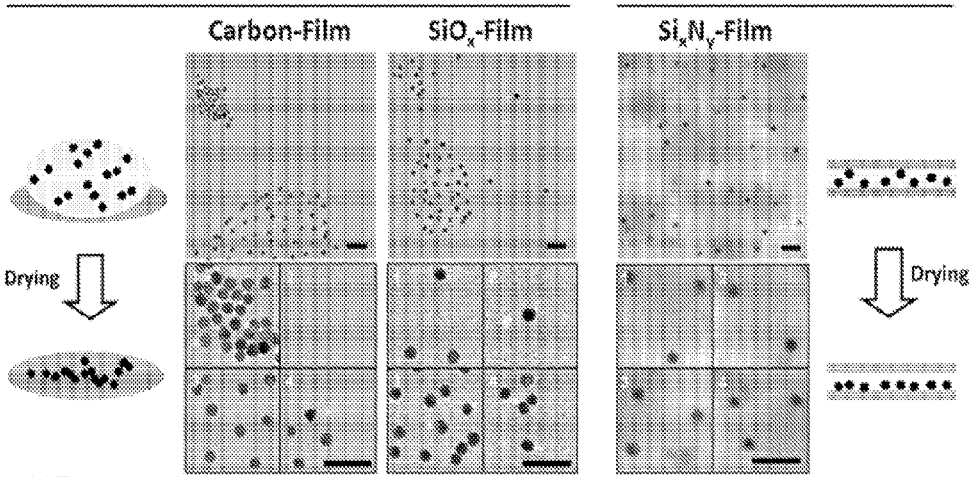
FIG. 11A
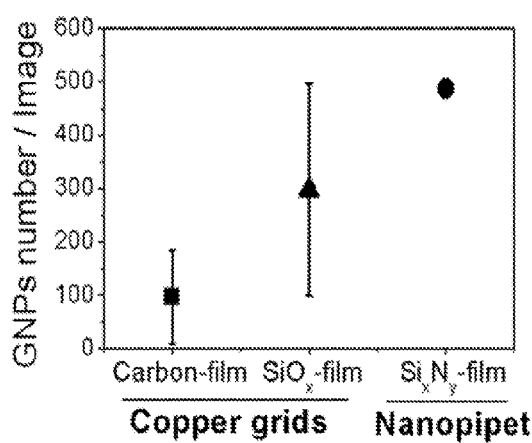
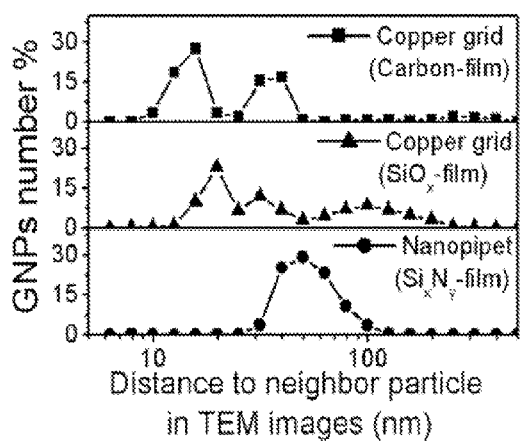
FIG. 11B  FIG. 11C

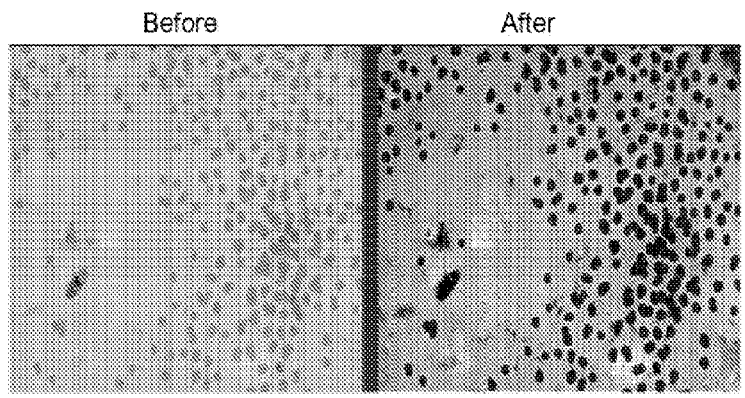
FIG. 15A  Before  After  FIG. 15B
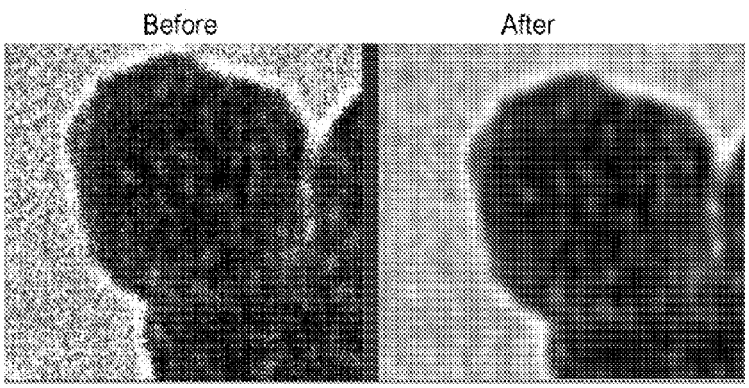
FIG. 15C  Before  After  FIG. 15D
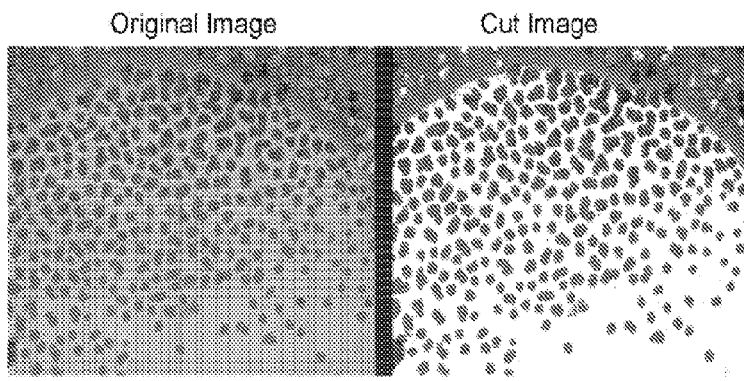
FIG. 15E  Original Image  Cut Image  FIG. 15F
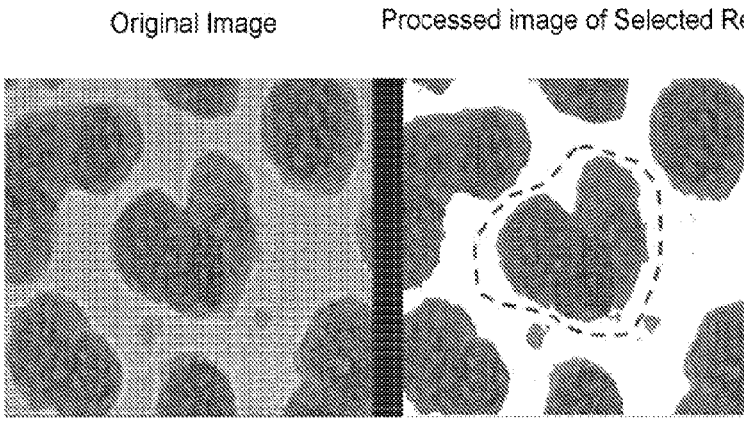
FIG. 15G  Original Image  Processed Image of Selected Region  FIG. 15H FIG. 15I
FIG. 15J
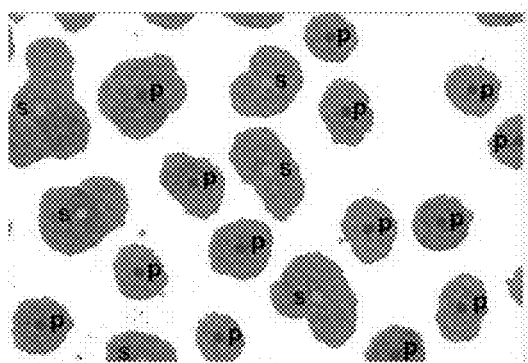
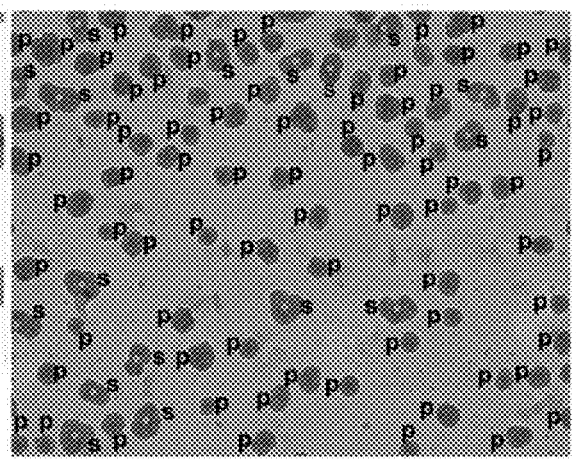
FIG. 16A
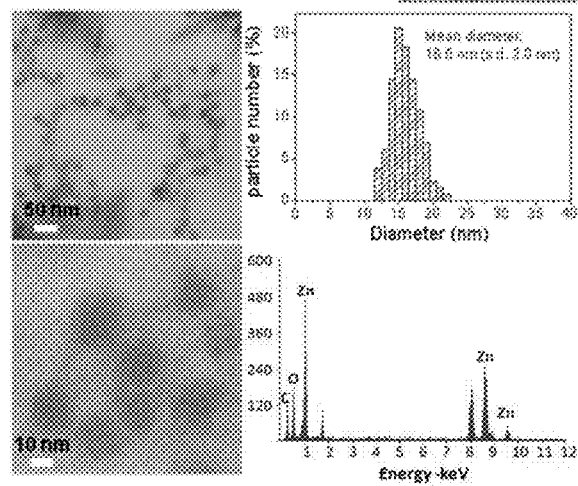
FIG. 16B
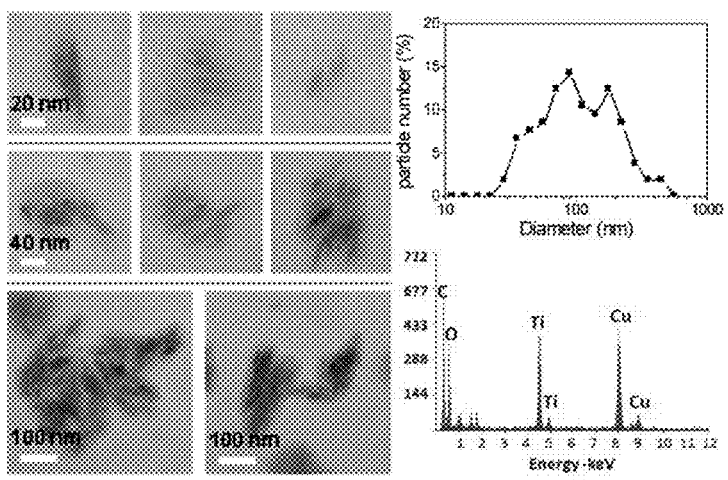

FIG. 17A
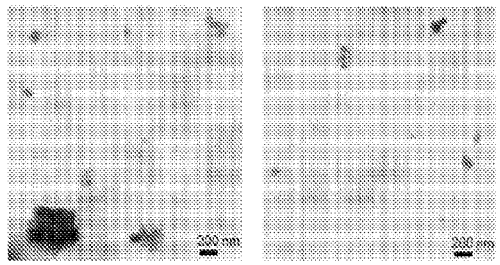
FIG. 17B
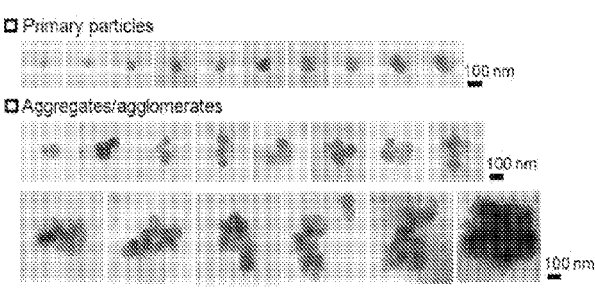
FIG. 17C
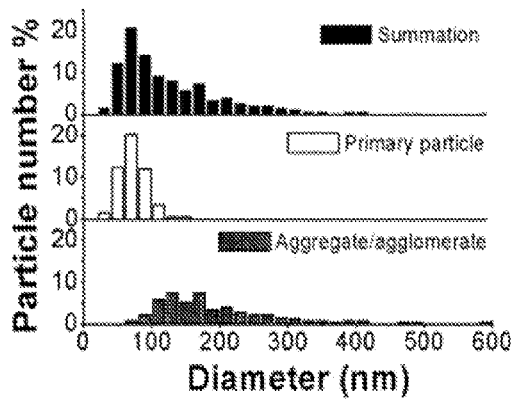
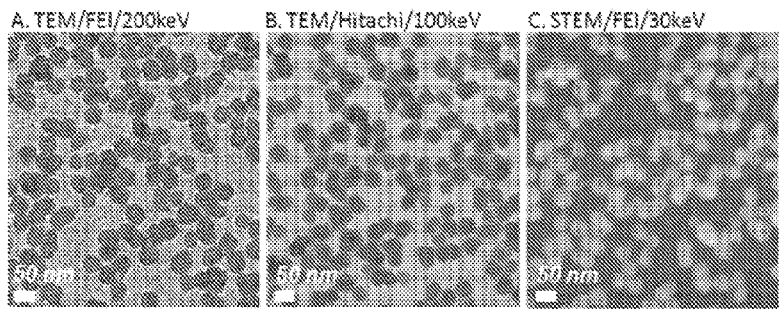
FIG. 18A
FIG. 18B
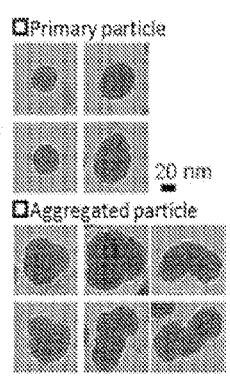
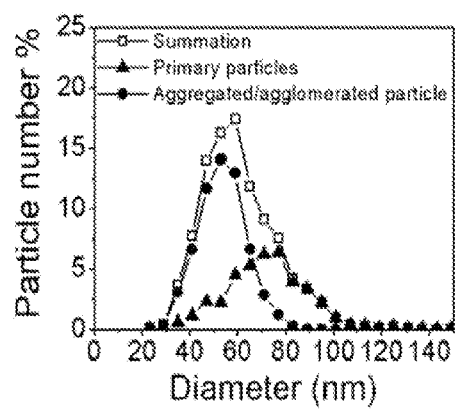

SPECIMEN PREPARATION FOR TRANSMISSION ELECTRON MICROSCOPY

REFERENCE TO RELATED APPLICATION

This application is a national stage application (under 35 U.S.C. 371) of PCT/US2013/049595 filed on Jul. 8, 2013, which claims priority to U.S. application Ser. No. 13/544,019 filed on Jul. 9, 2012, all of which are herein incorporated by reference in their entireties.

FIELD OF THE INVENTION

The present invention relates to a method for preparation of a specimen containing evenly distributed nanoparticles. Such an evenly distributed specimen is suitable for imaging-based observations and quantitative characterization using a transmission electron microscope (TEM). The invention facilitates real-time investigation of morphology, size, and dispersion of nanoparticles in a liquid sample, but without causing agglomerations of nanoparticles due to geometrical constraints of a specimen kit.

BACKGROUND OF THE INVENTION

Nanoparticles or nanoparticle-based formulations offer the advantage of efficient delivery to the target tissue for enhanced therapeutic or diagnostic purposes, which is usually related to their size, shape, surface properties, and aggregation/agglomeration states. Comprehensive physicochemical characterization of nanoparticles with respect to their size distribution, aggregation/agglomeration state, and shape in aqueous or physiological environments is important, yet challenging, for their use in biomedical applications and compliance with safety regulations. The aggregation/agglomeration of nanoparticles in biological fluids plays a critical role in determining the physical size, shape, and surface properties that are crucial for biological recognition, yet an image-based observation of such aggregation/agglomeration is difficult to achieve in a solid phase. Transmission electron microscope (TEM) is a unique and powerful tool for observing nanoparticles. However, due to the uneven spatial distribution of the nanoparticles in conventional TEM specimens, which are either prepared by drying the solution of nanoparticles onto copper grids or by freezing it on a cryostage holder, the TEM is rarely employed for evaluations of spatial distribution of nanoparticles in aqueous solutions.

SUMMARY OF THE INVENTION

The invention relates to fabrication of a microchip nanopipet with a controlled chamber width for sorting nanoparticles from a liquid samples such as a blood sample or milky phase liquid and preventing aggregation of the particles during a drying process, which enables quantitative analyses of their aggregation/agglomeration states and the particle concentration in an aqueous solution. This microchip is adaptable and compatible with all kinds of commercial TEM holders. Such a nanopipet proves to be a simple and convenient sampling device for TEM image-based quantitative characterization.

In one aspect, the invention relates to a method for preparing a specimen for TEM nanoparticle characterization, which comprises:
(a) providing a specimen kit containing:
   (i) a top substrate and a bottom substrate, each of the substrates having a top surface and a bottom surface and a length of L1, a width of W1, and a thickness of T1, the top and the bottom substrates being transparent and substantially parallel to each other;
   (ii) a first spacer and a second spacer, each having a length of L2, a width of W2, and a thickness of h, located beneath the top substrate and sitting on the bottom substrate, the second spacer being positioned opposite to and spaced apart from the first spacer at a distance of d, wherein the width of the spacer W2 is smaller than the width of the top substrate W1; and
   (iii) a non-enclosed chamber having two ends open to the atmosphere and formed between the top and bottom substrates and between the first and the second spacer, being characterized by having a length of L1, a width of d, and a height of h defined by the thickness of the spacer, wherein the height h being smaller than the diameter of a red blood cell; (Please provide ref. of image or schematic).
(b) loading a nanoparticle-containing liquid sample into the chamber; and
(c) drying the liquid sample within the chamber to obtain a dry specimen containing nanoparticles attached onto the bottom surface of the top substrate and the top surface of the bottom substrates.

In another aspect, the invention relates to a specimen kit as aforementioned.

In another aspect, the invention relates to a method for analyzing TEM images of nanoparticles a liquid sample, comprising: (Please quote ref figure to elucidate the following)
(a) preparing a dry specimen for TEM nanoparticle characterization according to the method as aforementioned;
(b) placing the dry specimen under a TEM; and
(c) observing and analyzing the TEM images of nanoparticles in the dry specimen to obtain information on aggregation, agglomeration and/or concentration of the nanoparticles in the liquid sample.

Further in another aspect, the invention relates to a system for use in analyzing TEM images of particles in a composition, comprising: (Please quote ref figure to elucidate the following)
(a) a specimen kit as aforementioned; and
(b) a computer software containing algorithms to perform the following functions:
   (i) acquiring TEM images of nanoparticles and storing the images in a computer;
   (ii) pre-processing the TEM images to enhance contrast, reduce noise and background;
   (iii) segmenting the nanoparticles in the images from the background;
   (iv) building a training database with a user interface; and
   (v) classifying the individual particles based on information in the training database.

In another aspect, the invention relates to a dry nanoparticle-containing specimen comprising nanoparticles in dry form evenly distributed within a non-enclosed chamber of a specimen kit as aforementioned; wherein the nanoparticles are loaded into the chamber as a non-dry particle form suspended in a liquid sample, and the nanoparticles in dry form evenly distributed within the chamber are attached onto the top surface of the bottom substrate and the bottom surface of the top substrate, and wherein the even distribution of the nanoparticles within the non-enclosed chamber reflects the status of the non-dry nanoparticles suspended in the liquid sample, and further wherein the dry specimen contains no cells. The top surface of the bottom substrate and the bottom surface of the top substrate forms part of the chamber's inner surfaces (the top and bottom inner surfaces).

These and other aspects will become apparent from the following description of the preferred embodiment taken in conjunction with the to drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF TILE DRAWINGS

FIGS. 1A~E are schematic side views (FIGS. 1A-D) and a top view (FIG. 1E) showing a conventional method for preparation of a microscopy specimen.

FIGS. 2A~E are schematic side views (FIGS. 2A-D) and a top view (FIG. 2E) showing a conventional method for preparation of another microscopy specimen.

FIGS. 3A-E are schematic side views (FIGS. 3A-D) and a top view (FIG. 3E) showing preparation of a dry microscopy specimen according to the invention.

FIGS. 4A~4E are schematic side views (FIG. 4A-D) and a top view (FIG. 4E) showing preparation of a microscopy specimen according to the invention.

Figure 7A:
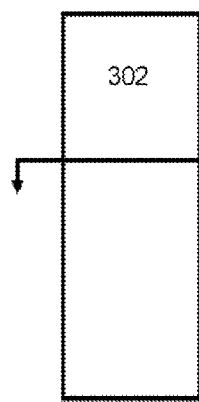
Figure 7B:
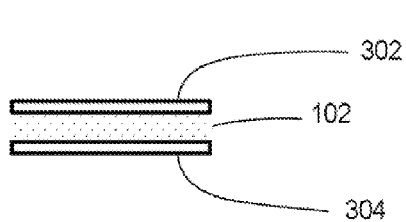

FIGS. 7A~7B are schematic top view (FIG. 7A) and cross-sectional view (FIG. 7B) of a specimen kit along line 702 according to one embodiment of the invention.

Figure 8A:
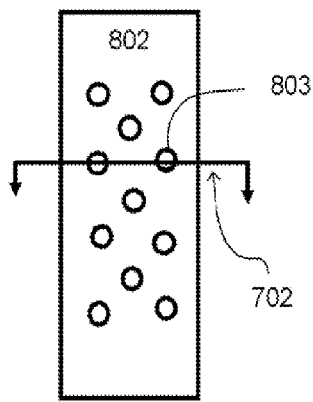
Figure 8B:
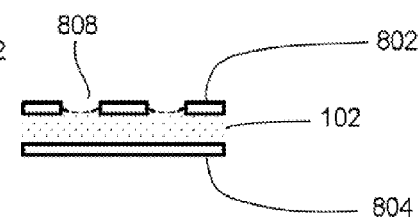

FIGS. 8A~8B are schematic top view (FIG. 8A) and cross-sectional view (FIG. 8B) of a specimen kit along line 702 according to another embodiment of the invention.

Figure 9A:
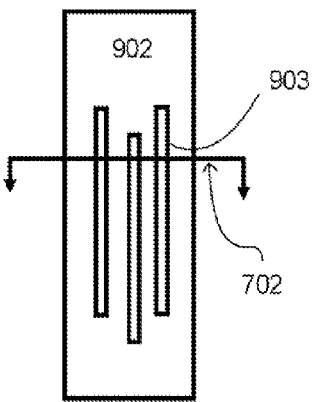
Figure 9B:
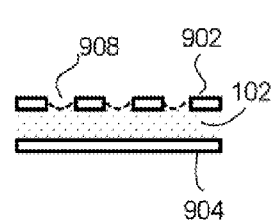

FIGS. 9A~9B are schematic top view (FIG. 9A) and cross-sectional view (FIG. 9B) of a specimen kit alone line 702 according to another embodiment of the invention.

FIG. 10 shows the geometry of the window-type TEM microchip nanopipet and sampling processes for specimen preparation: (A) schematic diagram of the device, with the dimensions and materials as indicated; (B) the nanopipet acts as a filter for simple and convenient sorting of nanoparticles to prevent entry of larger substances in the blood; (C) magnified schematic diagram of the chamber with a well-defined chamber width for controlling the drying processes.

FIG. 11 shows the drying processes and distribution of cPEG5k-GNPs on copper grids and the nanopipet: (A) TEM images of cPEG5k-GNPs in a 5% glucose solution dried on copper grids (with carbon and $SiO_x$ films) and in the nanopipet (with an $Si_xN_y$-film); (B) counted particle numbers in four individual image zones (2.0 μm×2.7 μm); (C) particle number percentage vs the distance to neighboring particles in the TEM images (sum of the four image zones). Scale bar is 50 nm.

FIG. 12 shows the observation of cPEG5k-GNPs in 50% diluted blood using the TEM nanopipet: (A) TEM images of the 5% glucose solution, the 50% diluted blood, and the cPEG5k-GNPs in the 50% diluted blood in the nanopipets; (B) particle number in the four nanopipets in the TEM image zones (2.0 μm×2.7 μm); (C) particle number percentage vs the distance to the neighboring particles in the four repeated blood samples in the nanopipets; (D) comparison of the particle number percentage vs distance to neighboring particles for the cPEG5k-GNPs in 50% blood and in 5% glucose. Scale bar is 20 nm.

FIG. 13 shows quantification of the cPEG5k-GNP concentration in blood samples using the TEM nanopipet and inductively coupled plasma-mass spectrometry (ICPMS) analyses: (A) concept for quantifying the concentration of nanoparticles using the nanopipet; (B) determination of the cPEG5k-GNPs concentration in 50% diluted blood using ICPMS and nanopipet (n=3). The blue line is the linear fitting result with a slope=1.03 ($C_{ICPMS}=C_{nanopipet}$) and $r^2$=0.997. (C) Determination of the cPEG5k-GNPs concentration in whole blood samples from a single rat at t=0.1, 1, 3, 7, 24, and 48 h using ICPMS (n=1) and the nanopipet (n=3) analytical methods. No significant difference was found between the two methods using the t test (p≤0.05) and (D) TEM images of the cPEG5k-GNPs in the whole blood of a rat. Scale bar is 20 nm.

Figures 14A, 14B:
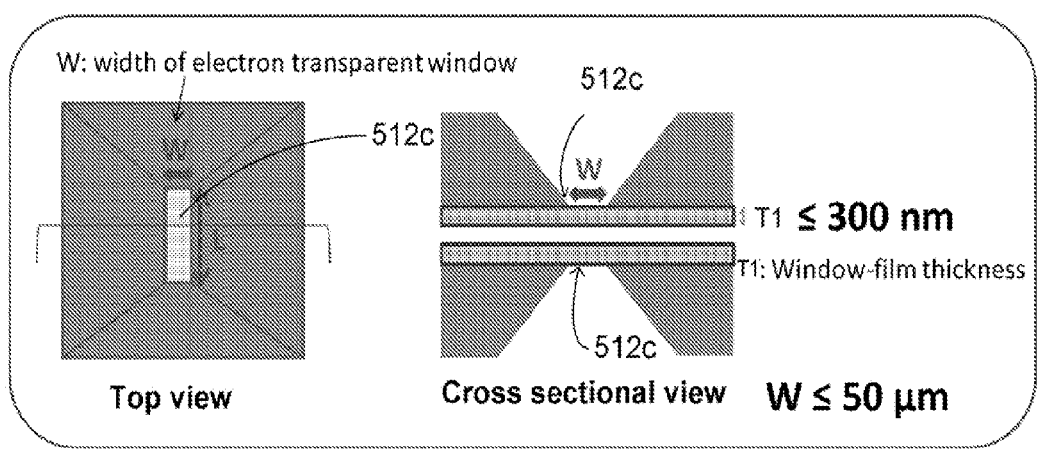

FIGS. 14A-B are schematic top view (FIG. 14A) and cross-sectional view (FIG. 14B) of a specimen kit along the line, showing the width of window vs. the thickness of the films (i.e., the top and bottom substrates).

FIGS. 15A-H show images before and after preprocess (FIG. 15A-D), segmentation (FIG. 15E-H), and particle selector for building database (FIG. 15I), and classification of images (FIG. 15J).

FIGS. 16A-B show the results of analyses of TEM images of ZnO and $TiO_2$ particles in sunscreen lotion.

FIGS. 17A-C show the results of analyses of TEM images of $CaCO_3$ particles in milk.

FIGS. 18A-B show the results of analyses of TEM images of CMP slurry.

DETAILED DESCRIPTION OF THE INVENTION

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The terms "specimen kit" and "microchip nanopipet" are interchangeable.

Particle aggregation refers to formation of dusters in a colloidal suspension and represents the most frequent mechanism leading to destabilization of colloidal systems.

Agglomeration refers to the sticking of particles to one another or to solid surfaces. Aggregation implies strong attractive forces and is irreversible; agglomeration is not as strong as aggregation and is more readily reversible, i.e., particles of the colloid are easier to break apart into smaller agglomerates or individual particles. Bare particles aggregate strongly. Surface-coated particles agglomerate eventually, but can be broken up readily.

As used herein, "nanoparticles" refers to particles of 1000 nm or less, and at least one dimension of the particles must be below 100 nm.

As used herein, when a number or a range is recited, ordinary skill in the art understand that it intends to encompass an appropriate, reasonable range for the particular field related to the invention.

By greater than 0.5 µm but less than 5 µm it meant that all tenth and integer unit amounts within the range are specifically disclosed as part of the invention. Thus, 0.6, 0.7, 0.8 and 1, 2, 3 and 4 µm unit amounts are included as embodiments of this invention.

By ranging from 50 nm to 300 nm it meant that all integer unit amounts within the range are specifically disclosed as part of the invention. Thus, 50, 51, 52, . . . , 298, 299, and 300 nm unit amounts are included as embodiments of this invention.

By ranging from 5 µm to 30 µm it meant that all integer unit amounts within the range are specifically disclosed as part of the invention. Thus, 5, 6, 7, . . . , 28, 29, and 30 µm are included as embodiments of this invention.

Energy Dispersive X-Ray Analysis (EDX), referred to as EDS or EDAX, is an x-ray technique used to identify the elemental composition of materials.

Support vector machines (SVMs, also support vector networks) are supervised learning models with associated learning algorithms that analyze data and recognize patterns, used for classification and regression analysis.

The terms "even distribution of nanoparticles" means the distance between neighboring nanoparticles exhibits an uniform Gaussian distribution as shown in FIG. 11C (sample preparation using nanopipet). FIGS. 11A-B (sample preparation using copper grid) show two distinct peaks, which represent large variations in distance between neighboring nanoparticles.

A specimen kit having a tiny chamber is disclosed for use in preparation of a specimen for TEM. The height of the chamber is smaller than the dimension of a blood cell and therefore is adapted to sort nanoparticles from blood cells. The specimen prepared according to the invention is suitable for TEM observations of the distribution status of nanoparticles in a liquid sample such as blood. The small height of the chamber eliminates the possibility of aggregation and/or agglomeration of the nanoparticles during drying. Thus, a specimen prepared under this invention is suitable for TEM observations of the dispersion and/or agglomeration of nanoparticles in a liquid sample.

In one aspect, the invention relates to a specimen kit (FIGS. 5, 6, 10, 14) comprising:
(a) a top substrate and a bottom substrate, each of the substrates having a top surface and a bottom surface and a length of L1, a width of W1, and a thickness of T1, the top and the bottom substrates being transparent and parallel to each other;
(b) a first spacer and a second spacer, each having a length of L2, a width of W2, and thickness of h, located beneath the top substrate and sitting on the bottom substrate, the second spacer being opposite to and spaced apart from the first spacer at a distance of d, wherein the width of the spacer W2 is smaller than the width of the top substrate W1; and
(c) a chamber formed between the top and the bottom substrates and between the first and the second spacers, the chamber having two ends open to the atmosphere and being characterized by having a length of L1, a width of d, and a height of h defined by the thickness of the spacer, wherein the height h being smaller than the diameter of a red blood cell.

In one embodiment of the invention, the top substrate further comprises a plurality of holes or channels or slits, the size of the holes or channels or slits is adapted to be sufficiently narrow so that a liquid sample within the chamber is restricted from leaking out/slipping through the holes or channels or slits in the top substrate.

In another embodiment of the invention, the top substrate does not contain hollow structures such as holes or slits or channels.

The bottom substrate of the specimen kit is flat and continuous without an hollow structures formed in the bottom substrate. The chamber is not enclosed nor sealed in all sides.

The length, the width and the height of the chamber is defined by the length of the top and the bottom substrates, the distance between the two spacers, and the thickness of the spacer, respectively. Therefore, the volume of the channel is fixed and can be calculated or determined. The length of the chamber according to one embodiment of the invention is no greater than 1 cm, and the height of the chamber is smaller than the diameter of a red blood cell.

In another embodiment of the invention, the aforementioned specimen kit further comprises:
(a) a top frame having a top surface and a bottom surface, the top frame being located on the top substrate and having an open window formed between the top surface and the bottom surface thereof; and
(b) a bottom frame having a top surface and a bottom surface, the bottom frame being located beneath the bottom substrate and having an open window formed between the top surface and the bottom surface thereof;
wherein each of the open windows has one window opening facing the chamber and another window opening facing away from the chamber, the window opening facing the chamber has a width not greater than 50 µm and a length not greater than 800 µm.

The top and bottom frames support the top and bottom substrates by providing strength to the substrates.

In another embodiment of the invention, the top and the bottom substrates each have a thickness ranging from 50 nm to 300 nm, or 50 nm~200 nm, preferably ranging from 100 nm~200 nm. It is important that the two substrates each have a thickness of no less than 50 nm to minimize deformation and to keep the top and bottom substrates (or films) in parallel during loading and drying of the liquid sample.

In another embodiment of the invention, the height of the chamber is larger than 0.1 µm but smaller than 5 µm. Alternatively, the height of the chamber is smaller than or equal to 5 µm. In another embodiment of the invention, the height of the chamber is selected from the group consisting of less than 10 µm, from 5 nm~2 µm, from 5 nm~0.5 µm, and from 5 nm~150 nm. In another embodiment of the invention, the chamber has a length of no greater than 1 cm, and a width of smaller than 1 cm.

In another embodiment of the invention, the top and bottom substrates each comprise a silicon nitride ($Si_xN_y$) film.

In another aspect, the invention relates to a specimen kit as aforementioned for use in preparing a dry specimen for transmission electron microscopy (TEM) nanoparticle characterization.

In another aspect, the invention relates to a method for preparing a specimen for TEM nanoparticle characterization, which comprises: (a) providing a specimen kit as aforementioned; and (b) loading a nanoparticle-containing liquid sample into the non-enclosed chamber. In this case, the method does not include a drying process and thus the nanoparticles in the liquid sample is observed under TEM.

Further in another aspect, the invention relates to a method for preparing a specimen for TEM nanoparticle characterization, which comprises:
(a) providing a specimen kit as aforementioned;
(b) loading a nanoparticle-containing liquid sample into the non-enclosed chamber; and
(c) drying the liquid sample within the non-enclosed chamber to obtain a dry specimen containing nanoparticles attached onto the bottom surface of the top substrate and onto the top surface of the bottom substrate.

In one embodiment of the invention, the loading step is performed by positioning one end of the chamber downward to contact with the liquid sample.

In another embodiment of the invention, the nanoparticle-containing liquid sample is at least one selected from the group consisting of a blood sample, a bodily fluid, a lotion, a chemical mechanical polishing/planarization slurry, and a calcium carbonate nanoparticle-containing liquid or milk.

In another embodiment of the invention, during drying of the liquid sample the nanoparticles are restricted from movement and aggregation and/or agglomeration.

Further in another aspect, the invention relates to a method for analyzing TEM images of nanoparticles in a liquid sample, which comprises
(a) preparing a dry specimen for TEM nanoparticle characterization according to a method as aforementioned;
(b) placing the dry specimen under a TEM; and
(c) observing and analyzing the TEM images of nanoparticles in the dry specimen to obtain information on aggregation, agglomeration and/or concentration of the nanoparticles in the liquid sample.

In one embodiment of the invention, the observing and analyzing step further comprises:
(i) acquiring TEM images of the nanoparticles and storing the TEM images in a computer;
(ii) preprocessing the TEM images to enhance contrast, reduce noise and background
(iii) segmenting the nanoparticles hi the images from the background;
(iv) building a training database with a user interface; and
(v) classifying the individual particles based on information in the training database.

In another embodiment of the invention, steps (i)~(v) are performed with a computer software.

In another embodiment of the invention, the building step comprises training the computer to recognize properties of nanoparticles. The properties may be at least one selected from the group consisting of aggregated particles and single particles.

In another aspect, the invention relates to a system for use in analyzing TEM images of particles in a composition, wherein the system comprises:
(a) a specimen kit as aforementioned; and
(b) a computer software having algorithms to perform the following functions:
(i) acquiring TEM images of nanoparticles and storing the images in a computer;
(ii) preprocessing the TEM images to enhance contrast, reduce noise and background
(iii) segmenting the nanoparticles in the images from the background;
(iv) building a training database with a user interface; and
(v) classifying the individual particles based on information in the training database.

The support vector machines (SVM) are algorithms that may be adapted to perform preprocessing, segmenting, training database-building and particle-classification. Pre-processing step employs the following histogram equalization algorithm:

$$p_x(i) = \frac{n_i}{n}$$

$$cdf_x(i) = \sum_{j=0}^{i} p_x(j)$$

$$k = cdf_x(x)$$

Yet in another aspect, the invention relates to a dry nanoparticle-containing specimen characterized by an even distribution of nanoparticles within a non-enclosed (or non-closed) chamber of a specimen kit as aforementioned, the dry specimen resulting from drying of a nanoparticle-containing liquid sample, wherein the even distribution of the nanoparticles within the non-enclosed chamber reflects the status of the nanoparticles in the liquid sample. The nanoparticles-containing specimen is not enclosed or is non-closed. The nanoparticle-containing liquid sample may be at least one selected from the group consisting of a blood sample, a bodily fluid, a lotion, a chemical mechanical polishing/planarization slurry, and a calcium carbonate nanoparticle-containing liquid or milk.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Microscopy Specimen Prepared by Conventional Methods

FIGS. 1A-E are schematic drawings illustrating a conventional method for preparation of a microscopy specimen. A drop of biological fluid sample 102, e.g., a blood sample, which contains blood cells 104 and particles 106, e.g., nanoparticles, is placed on a piece of substrate 100 such as a copper grid (FIGS. 1A-B, side views). The diameter of a nanoparticle is usually no greater than 1 micrometer and thus, is smaller than the diameter of a blood cell. A red blood cell (RBC) has an average diameter of 6~8 µm, and a white blood cell (WBC) has an average diameter of 10~12 µm. The liquid in the biological fluid or blood sample 102 evaporates during a drying process, which causes shrinkage of the liquid drop and formation of a plurality of smaller droplets (FIG. 1C, a side view). A surface tension 108 within each droplet drags the components, e.g., nanoparticles, therein closer and closer to each other, resulting in aggregation of the nanoparticles within the droplets. FIG. 1D (a side view) illustrates two aggregation groups 110a and 110b formed after the liquid in the sample is completely evaporated. The aggregation of nanoparticles 110a and 110b which occur in the above prepared specimen displays a similar appearance to nanoparticle-agglomeration, which causes observation confusions between nanoparticle aggregation and nanoparticle agglomeration and gives a TEM observer inaccurate or fake information. FIG. 1E is a top view of FIG. 1D, showing two aggregation groups 110a and 110b formed. The microscopy specimen of FIG. 1E does not reflect the true status of the nanoparticles 106 in the original sample 102 because the nanoparticles 106 in the original sample 102 are evenly dispersed without any aggregation (FIG. 1B). This would frustrate the purpose for using a TEM to obtain information on the status, dispersion and/or agglomeration of nanoparticles in a blood sample from a subject.

FIG. 2 is another illustration of a microscopy specimen prepared according to a conventional method. A drop of biological fluid sample 102, e.g., a blood sample, which contains blood cells 104, dispersed nanoparticles 106 and nanoparticle agglomerations 210, is placed on a piece of substrate 100 such as a copper grid (FIGS. 2A-B). The liquid in the blood sample 102 evaporates during a drying process, which causes shrinkage of the liquid drop and formation of a plurality of smaller droplets (FIG. 2C). A surface tension 108 within each droplet drags the components, e.g., nanoparticles, therein closer and closer to each other, resulting in formation of aggregation 110a and 110b of the nanoparticles within the droplets (FIG. 2D). FIG. 2E is a top view of FIG. 2D, showing two aggregation groups 110a and 110b, which are newly formed aggregations because they do not exist in the original blood sample 102 (FIG. 2B). Thus, the microscopy specimen prepared according to FIG. 2 would give false information to a TEM observer.

The microscopy specimen shown in FIGS. 2D-E present nanoparticle agglomeration 210, and newly formed nanoparticle aggregations 110a and 110b, which have similar appearance as nanoparticle agglomeration 210. The newly formed nanoparticle aggregations 110a and 110b are caused by a surface tension 108 within the droplets during the process of drying. This would frustrate the purpose for using TEM to obtain information on whether an original blood sample contains nanoparticle agglomerations or not since the microscopy specimen prepared with the conventional method does not reflect the true number of nanoparticle agglomerations.
Microscopy Specimen Prepared with a Microchip Nanopipet (i.e., a Specimen Kit)

This invention relates to a microcopy specimen prepared with a microchip nanopipet that has a tiny chamber. The height of the chamber is configured to be much smaller than the diameter of a red blood cell (RBC). A RBC is smaller than a WBC. Thus, all the blood cells can be excluded/screened from entering the chamber of the microchip nanopipet. The absence of the blood cells in the specimen reduces interference with observations of nanoparticles and therefore enhances the quality and quantity examinations of the specimen. The small chamber of the microchip nanopipet holds the blood sample within, and eliminates the effect of a surface tension during a drying process. A microscopy specimen prepared according to the invention makes it possible to detect the true distribution status of the nanoparticles such as the dispersion and/or agglomeration in the original blood sample.

FIG. 3 illustrates preparation of a microscopy specimen according to the invention. A blood sample 102 is caused to contact with one end of a chamber 300 formed between a top substrate 302 and a bottom substrate 304 (FIG. 3A) of a microchip nanopipet. The blood sample 102 contains nanoparticles 106 and blood cells 104. The height h between the top substrate 302 and the bottom substrate 304 is made to be less than the diameter of a red blood cell 104 so that all the RBCs and WBCs are excluded from entering the chamber 300. The top substrate 302 has a top surface 306 and a bottom surface 307. The bottom substrate 304 also has a top surface 310 and a bottom surface 312. A height h of 10 µm for the chamber 300 is sufficient for TEM observations of distribution status, dispersion and/or agglomeration, of nanoparticles in a blood sample.

The nanoparticles 106 along with blood fluid enter a chamber 300 (FIG. 3B). The blood cells 104 are excluded from entering into the chamber 300 due to the cell size being bigger than the chamber's height. The liquid inside the chamber undergoes a drying process, which causes formation of a plurality of small droplets. Each droplet wraps a single nanoparticle 106 and attaches onto the inner surfaces (i.e., the bottom surface of the top substrate and the top surface of the bottom substrate) of the chamber 300 due to an adhesion force 308 of the droplet (FIG. 3C). FIG. 3D is a side view of a microscopy specimen after the liquid in the blood sample is dried, which shows some nanoparticles 106 attached to the bottom surface 307 of the top substrate 302, and some nanoparticles 106 attached to the top surface 310 of the bottom substrate 304. Because of the tiny space or the small height h between the two substrates 302, 304, the number of nanoparticles 106 distributed in a thin sample layer (H) is limited, which eliminates the possibility of aggregations of nanoparticles 106 in a thin sample layer (H). FIG. 3E is a top view of FIG. 3D, showing that the dispersed nanoparticles 106 truly reflect a real dispersion status of the nanoparticles 106 in the original blood sample 102 as shown in FIG. 3B.

FIG. 4 illustrates preparation of another microscopy specimen according to the invention. A blood sample 102 is caused to contact with one end of a chamber 300 formed between a top substrate 302 and a bottom substrate 304 (FIG. 4A) of a microchip nanopipet. The blood sample 102 contains nanoparticle agglomerations 210, dispersed nanoparticles 106 and blood cells 104. The height h between a top substrate 302 and a bottom substrate 304 is made to be less than the diameter of a red blood cell 104 so that all the RBCs and WBCs are excluded from entering the chamber 300. Both nanoparticles 106 and nanoparticle-agglomeration 210 enter the chamber 300 along with the fluid of the blood sample 102. Blood cells 104 cannot enter the chamber 300 due to its dimension being larger than the height of the chamber (FIG. 4B). The liquid inside the chamber undergoes a drying process, which causes formation of a plurality of small droplets. Each droplet wraps a single nanoparticle 106 or a group of agglomerated nanoparticles 210 and attaches onto the inner surfaces (i.e., the bottom surface of the top substrate and the top surface of the bottom substrate) of the chamber 300 due to an adhesion force 308 of the droplet (FIG. 4C). After the liquid within the chamber 300 is complete dry, some dispersed nanoparticles 106 and nanoparticle-agglomeration 210 are attached to the bottom surface of the top substrate 302 and to the top surface of the bottom substrate 304. The tiny space or the small height h limits the number of the nanoparticles 106 and nanoparticle-agglomeration 210 distributed in a thin sample layer (H), and hence eliminates the possibility of aggregation of the nanoparticles 106 and the nanoparticle-agglomeration 210 a thin sample layer (H) (FIG. 4D). FIG. 4E is a top view of FIG. 4D, in which the dispersed nanoparticles 106 and nanoparticle-agglomeration 210 of the microscopy specimen truly reflect the real situation of nanoparticles 106 and nanoparticle-agglomeration 210 distributed in an original blood sample 102 as shown in FIG. 4B.

Figure 5:
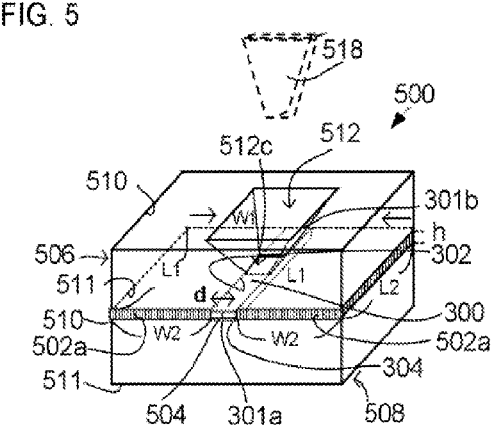
FIG. 5 is a schematic perspective view of a specimen kit (or a microchip nanopipet) according to one embodiment of the invention.

FIG. 5 illustrates a microchip nanopipet 500 for use in preparing a microscopy specimen for observations under a TEM. The microchip nanopipet 500 has a chamber 300 formed in between a top substrate 302 and a bottom substrate 304; wherein the height h of the chamber 300 is smaller than the diameter of an RBC, and the top substrate 302 is made of a material that is transparent to electrons. A chamber height of less than 10 µm is sufficient to allow TEM observations of the distribution status of nanoparticles, and dispersion or agglomeration of nanoparticles in a blood sample 102. A first spacer 502a and a second spacer 502b are inserted between the top 302 and bottom 304 substrates to control the height of the chamber 300. The chamber 300 has a first 301a end and a second end 301b, each of the ends has an entrance 504. The entrance 504 may be configured for injection of a sample.

Figure 6:
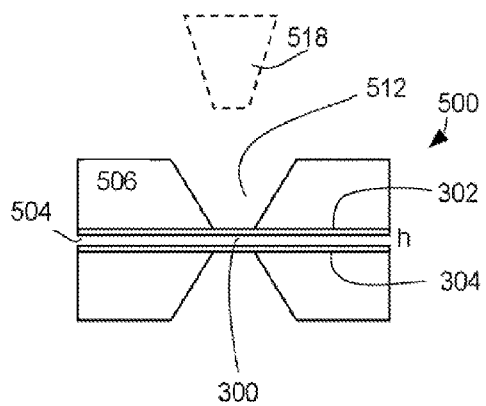
FIG. 6 is a schematic cross-sectional view of a specimen kit (a microchip nanopipet).

A top frame 506 is located on a top substrate 302, and a bottom frame 508 (which may be of the same size as the top frame) is located beneath a bottom substrate 304, wherein the top frame 506 and the bottom frame 508 each have a top surface 510 and a bottom surface 511, and an open window 512 formed between the top 510 and the bottom 511 surfaces, the open window 512 having a height $h_w$ equal to the thickness of the top 506 or the bottom 508 frame, and a length and a width both smaller than the length and the width of the top or bottom frame. The open window 512 receives TEM electron Beam 518 (FIGS. 5~6).

The open window 512 in the top frame 506 and the open window 512 in the bottom frame 508 each have an opening 512c facing the chamber and another opening, facing away from the chamber (FIG. 10A). The opening 512c (which faces the chamber) of the top frame open window is formed at the bottom surface of the top frame, facing toward the top substrate 302 and thus the chamber 300. The opening 512c of the bottom frame open window is formed at the top surface of the bottom frame, facing toward the bottom substrate 304 and the chamber 300. The opening 512c facing the chamber has a width 516 of no greater than 50 µm, and a length 514 of no greater than 800 µm. Therefore, the particle specimen within the chamber 300 may be observed through the window opening 512c (which is located at the bottom surface of the top frame and faces the top substrate 302 and the chamber 300) under a TEM from the top of the microchip nanopipet 500.

The thickness of the top and bottom substrates ranges from 50 nm to 300 nm, or 50 nm~200 nm, preferably in a range of 100 nm~200 nm.

The thickness of the substrates and the width of the window are highly important for use of the specimen kit in TEM image-analyses of nanoparticles according to the invention. The two substrates each need to have a thickness of no less than 50 nm, and the window width 516c facing the chamber (i.e., the window opening that faces the chamber) needs to be less than or equal to 50 µm. These requirements are necessary to minimize deformation of the top and bottom substrates and to keep the top and bottom substrates (or films) in parallel. The deformation of the substrates (or films) would result in aggregation of particles during a drying process, and incorrect TEM image analysis of nanoparticles.

FIGS. 14A-B illustrate the dimensions of the width (w) of the open window 512c facing the chamber and the thickness of the film (the top and bottom substrates). The dimensions need to be in a certain range so that the two films (i.e., top and bottom substrates) at the portion adjacent to (or exposed to) the open windows 512c remain parallel to each other. The width of the open window 512c facing the chamber is ≤50 µm, preferable 5-30 µm, and the length is ≤800 µm, preferable 50-500 µm. The thickness of the film (or substrate) is ≤300 nm, preferable 50-200 nm.

FIG. 6 shows a chamber 300 formed between a top substrate 302 and a bottom substrate 304. An observation window 512 is made at the center of the top frame 506 of the microchip nanopipet 500. Part of the chamber 300 may be observed through the window 512 under a TEM from the top of the microchip nanopipet 500. One end of the chamber 300 serves as an entrance 504 for a liquid sample.

FIG. 7A shows a top view over the chamber 300. A top substrate 302 is made of a tint panel and is transparent to electrons FIG. 7B is a cross-section view of FIG. 7A, showing both the top substrate 302 and the bottom substrate 304, and a liquid sample, e.g., blood, 102 is filled into the chamber 300 between the substrates 302 and 304.

FIG. 8 illustrates a microchip nanopipet according to another embodiment of the invention. FIG. 8A is a top view of a top substrate 802 containing holes 803 in another microchip nanopipet, showing a plurality of holes 803 penetrating through the top substrate 802. Observations of a specimen may be made with blood or liquid in the chamber. A better quality of observation of the specimen with a TEM may be made through the holes 803 without hindrance of the top substrate 802. FIG. 8B is a cross-sectional view of FIG. 8A, showing the top substrate 802 and the bottom substrate 804, a sample blood 102 filled into a chamber between the substrates 802, 804. Each hole is configured to be small enough to hold a blood sample 102 within the chamber by a surface tension 808 so that the blood sample liquid 102 does not seep through the hole 803.

FIG. 9 illustrates a microchip nanopipet according to another embodiment of the invention. FIG. 9A is a top view of a top substrate 902 containing slits or channels 903 in another microchip nanopipet, showing a plurality of slits or channels (or penetrating grooves) 903 penetrating through the top substrate 902. Observations of a specimen may be made with blood or liquid in the chamber. A better quality of observation of the specimen with a TEM may be made through the slits 903 without hindrance of a top substrate 902. FIG. 9B is a cross-sectional view of FIG. 9A, showing a top substrate 902 and a bottom substrate 904, a sample blood 102 filled into a chamber between the substrates 902, 904. Each slit or channel is configured to have a width small or narrow enough to hold a blood sample 102 within the chamber by a surface tension 908 so that the blood sample liquid 102 does not seep through the slits 903.

Here, a microchip nanopipet with a narrow chamber width was constructed to prevent the aggregation of the particles during a drying process, enabling a quantitative analysis of their aggregation/agglomeration states and particle concentration in blood (FIG. 10). The upper substrate of the nanopipet breaks the surface tension of the sample droplet, suppressing the capillary flow accompanied with evaporation of water and the aggregation of the substances when the droplet is conventionally dried on a copper grid. This nanopipet acts as a filter for simple and convenient sorting of PEGylated gold nanoparticles in whole blood, 50% diluted blood, and 5% glucose solution. The slight aggregation of carboxyl-PEG5k-modified gold nanoparticles (~18%) in a 50% diluted blood sample was observed while they were well-dispersed in a 5% glucose solution. Moreover, a consistent concentration for the cPEG5k-GNPs was obtained using the nanopipet and inductively coupled plasma-mass spectrometry (ICPMS) analysis for both in vitro 50% diluted blood and in vivo whole blood.

We examined the possibility of the use of a nanopipet to obtain the aggregation/agglomeration states of particles in aqueous solutions. Carboxyl-PEG5k-modified gold nanoparticles (cPEG5k-GNPs), which are known to be long circulating and in a well-dispersed colloidal form in blood, were dissolved in 5% glucose solution and used as model particles for examining and comparing the spatial distribution of the particles in TEM specimens dried in the nanopipet (with an $Si_xN_y$-film) and on copper grids (with either a carbon-film or an $SiO_x$-film). An even spatial distribution of the particles was observed in the nanopipet with an $Si_xN_y$-film (water contact angle: ~32°), with the particle number in four randomly chosen 2.0 μm×2.7 μm image zones determined to be 478, 467, 502, and 504 (FIGS. 11A-B). The distance of each cPEG5k-GNP to the nearest adjacent particle (FIG. 11D) was also measured for all four of the 2.0 μm×2.7 μm image zones, and the particle number percentage (n/N) was plotted versus the distance to the neighboring particle (FIG. 11D). A single broad distribution peak was observed with a mean distance of 69.4±21.6 nm (FIG. 11C), which is larger than the diameter of cPEG5k-GNP (~39.6 nm as observed by TEM, ~39.3 nm as measured by DLS), and indicates that most of the particles are separated from the neighboring particles. The higher percentage of particles distributed at d values greater than the particle diameter suggests that most of the particles are distributed without contact and separated without aggregation. These results are in accordance with the understanding of cPEG5k-GNPs, which are well-dispersed in 5% glucose solution, and indicate that the nanopipet can preserve the native spatial distribution of the particles and avoid aggregation/agglomeration in the sample solution. However, when the same sample solution was dried on the copper grid with a hydrophobic carbon-film (water contact angle: ~70°) and even on the grid with a hydrophilic $SiO_x$-film (water contact angle: ~30°), an obvious uneven spatial distribution of the particles was observed (FIGS. 11A-B). From the plot of the particle number percentage vs distance to the neighboring particle (FIG. 11D), three peaks were obtained for both the carbon-film and $SiO_x$-film copper grids (FIG. 11C). Note: Figure caption in PDF file should be edited. It should be "Distance to neighboring particle . . . " The presence of two peaks with a distance smaller than the diameter of the cPEG5k-GNPs suggests that the particles are vertically stacked or self-aggregated on the copper grids during the drying process (gradual evaporation of the bulk solvent), and even the hydrophilic surface modification with an $SiO_x$-film cannot prevent aggregation. In another example, 300 nm polystyrene beads were dried both in nanopipets and on copper grids. The beads were well separated in the nanopipets but highly aggregated on the copper grids (carbon film and $SiO_x$ film). The nanopipet clearly offers a simple and convenient sampling device for preserving and quantifying the native aggregation/agglomeration states of the particles, which are free of any artifacts introduced due to the sampling device.

Figure 12A:
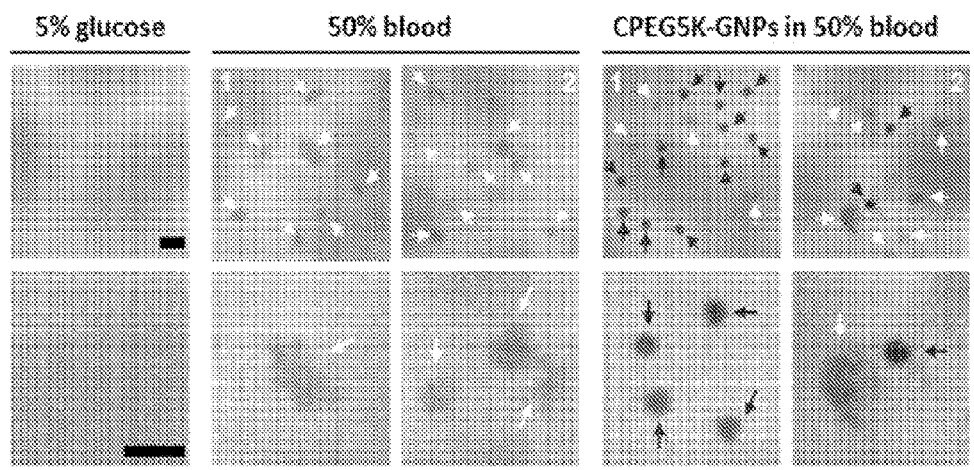
Figure 12B:
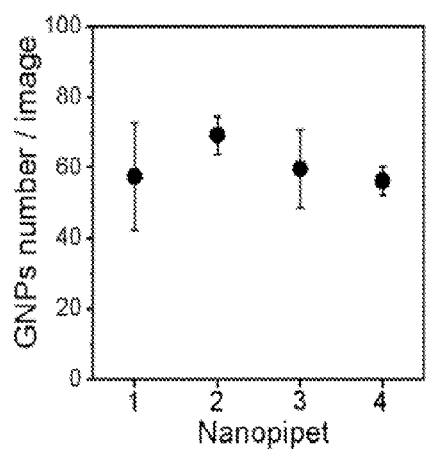
Figure 12C:
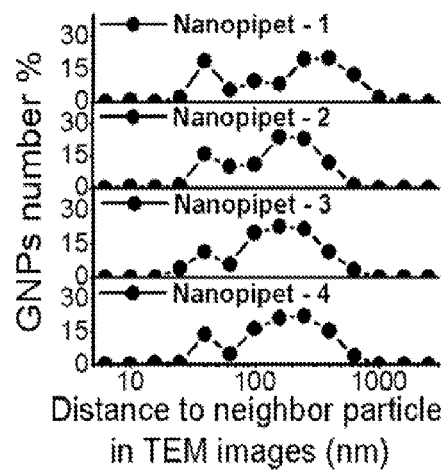
Figure 12D:
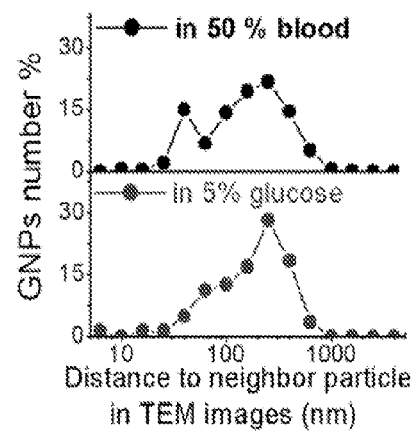

Furthermore, we examined the possibility of the use of a nanopipet with a well-defined chamber width to sort out certain-sized particles from blood, which is an interesting physiological environment in which the observation and characterization of nanoparticles is challenging. In addition to preserving the native spatial distribution of the particles, the defined narrow chamber structure of the nanopipet can also act as a filter for simple and convenient sorting of nano-sized materials, preventing the entry of larger substances found in blood; in this case, the blood cells and platelets can be excluded in the sample loading process (FIG. 10B). Thus, only the submicrometer sized particles in blood plasma smaller than the chamber width of the nanopipet were sampled and observed by TEM. A 50% diluted blood sample was studied using this method, and some irregular-shaped nanoscale substances (5-20 nm) were observed that might be serum proteins, such as serum albumin (FIG. 12A). When cPEG5k-GNPs were spiked into the 50% diluted blood, both the gold nanoparticles (indicated with the purple arrow) and the presumed blood proteins (indicated with the white arrow) were easily visualized, recognized, and used for image-based quantitative analysis (FIG. 12A). Four nanopipets were used to load the particles from the same 50% diluted blood sample, and a similar particle number was observed for each (FIG. 12B). The even spatial distribution of the particles and the reproducible quantitative results reveal that the nanopipet is a promising sampling device for sorting particles from blood. Moreover, the aggregation/agglomeration states of the cPEG5k-GNPs in the 50% diluted blood were evaluated by plotting the particle number percentage vs the distance to the neighboring particles (FIG. 12D). In FIG. 12C, four repeated trials showed that the cPEG5k-GNPs exhibited a broad peak (~80% particles) with distances to the neighbor particles that were larger than the diameter of the cPEG5k-GNPs, indicating that most of the particles were well dispersed in the blood. A small additional peak appearing near the diameter of the cPEG5k-GNPs (~39.6 nm) with particle number percentages of 21.7%, 18.4%, 15.4%, and 15.6% was also observed for all four of the repeated nanopipets. Because only a single peak was observed when the same concentration of cPEG5k-GNPs was spiked into a 5% glucose solution, the additional aggregation peak with a particle number of 18% reveals that the 50% diluted blood induces a slight aggregation of the particles (FIG. 12D). The results confirm that the nanopipet offers a simple and convenient sampling device for sorting nanoparticles and estimating the aggregation/agglomeration states of nanoparticles in blood with reproducible and quantitative results and can also be used for the analysis of other biological fluids of interest. Moreover, intentionally aggregated, citrate-modified gold nanoparticles (citrate-GNPs) were examined. In 5% glucose, the citrate-GNPs showed ~70% aggregation with 2-10 nanoparticles in each aggregate, while in 50% diluted blood, the extent of aggregation of the particles increased to ~87%, with ~40% of the aggregates containing 11-100 particles in each aggregate. The nanopipet may, therefore, potentially be able to distinguish the aggregation extent of intentionally aggregated nanoparticles in different aqueous environments.

Figure 13A:
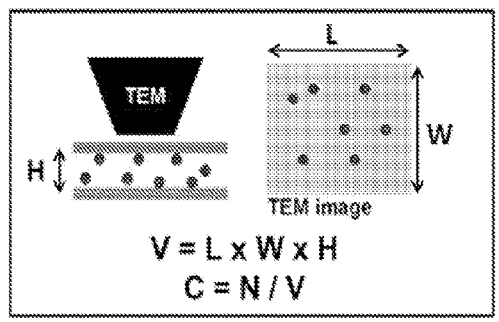
Figure 13B:
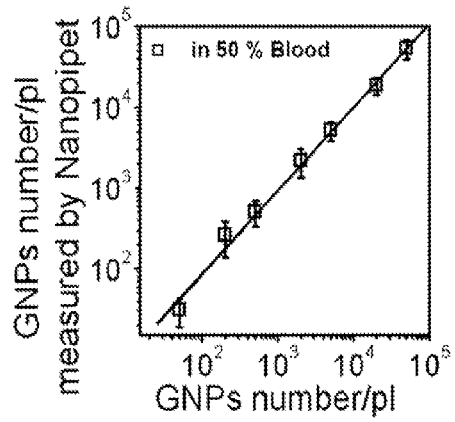
Figure 13C:
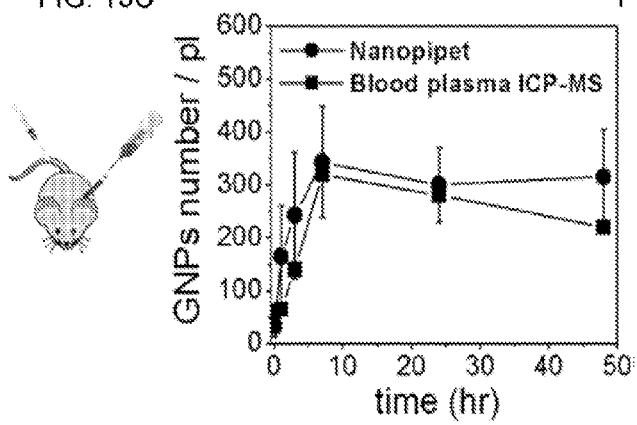
Figure 13D:
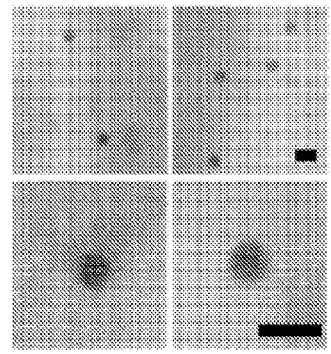

Quantifying the concentration of nanoparticles in a biological matrix is important for in vivo analysis of their absorption, distribution, metabolism, and excretion, as well as for pharmacokinetic and toxicity studies, particularly for nanoparticles composed of elements that are abundant in the biological fluids in the body (e.g., C, H, O, N, P, Fe, Zn, and Ca) yet still remains a common challenge. In addition to preserving the native spatial distribution of the particles in order to prepare a homogeneous specimen and act as a filter for sorting particles from blood, the fixed and well-defined narrow chamber volume of the nanopipet has an image volume (V) equal to the TEM image area multiplied by the chamber width of the nanopipet (V=L×W×H). The particle number (N) in each TEM image was thus counted and divided by the total imaged volume to determine the particle concentration (C) in each sample solution (C=N/V) (FIG. 13A). The number of cPEG5k-GNPs in the nanopipet counted in the TEM images was then compared to the ICPMS analysis, which is the gold standard method for quantifying the concentration of metals (such as Au, Ag, Fe, etc.). The particle concentration of the cPEG5k-GNPs counted in the nanopipets (n=3) and calculated by ICPMS are consistent in the particle concentration range from $5\times10^{10}$ to $5\times10^{13}$ particles/mL in 50% diluted blood (FIG. 13B). Furthermore, cPEG5k-GNPs in 5% glucose (400 μL, $3\times10^{14}$ particles/mL) were injected intravenously in a rat, and blood samples were collected following injection (t=0.1, 1, 3, 7, 24, 48 h). Each whole blood sample was sorted using nanopipets (n=3) and analyzed by ICPMS. FIG. 13C shows the comparable results obtained for the number of cPEG5k-GNPs counted in the nanopipets and measured by ICPMS. This experiment confirmed that the nanopipet is a simple and convenient sampling device for evaluating the concentration of nanoparticles using TEM. The success is attributed to the ultra small sample volume required (<1 μL), and this tool may be used to analyze the particle concentration in local body fluids of interest.

In conclusion, we have constructed a microchip-based nanopipet for the preparation of homogeneous specimens and the sorting of nanoparticles from blood. In addition to morphology based information, a TEM image-based quantitative method was developed for analyzing the shape, size/size distribution, aggregation/agglomeration states, and concentration of particles in aqueous environments of interest. Moreover, this nanopipet is adaptable to all TEM holders, mass producible, disposable, and convenient for sample loading and observations. A comprehensive physiological characterization of PEGylated gold nanoparticles, including their aggregation/agglomeration state and number of particles in a blood sample demonstrates the potential of this nanopipet device for nanoparticle characterization in biological fluids. Because the characterization is based on observations of individual particles, this method can be easily extended to other particle-based materials, particularly for quantifying nanoparticles composed of the elements that are abundant in biological fluids (e.g., C, H, O, N, P, Fe, Zn, and Ca). In addition to observations under dry conditions, the sorted thin layer sample solution may be sealed in nanopipets and imaged in the native aqueous environment. In this study, therefore, we demonstrated that our nanopipet, a simple and conventional sampling device, offers the possibility of the use of TEM to quantitatively characterize the size/size distribution, shape, aggregation/agglomeration state, and particle concentration of nanomaterials in various native environments of interest.

A computer software was used to analyze nanoparticle images. TEM images of the nanoparticles were acquired and stored in a computer, and then preprocessed to enhance contrast (FIG. 15A-B) and reduce noise and background (FIG. 15C-D). The nanoparticles in the images were then segmented from the background (threshold image cut). The user or observer then builds a training database with a user interface (particle selector to select primary particle and secondary particle (FIG. 15G). Finally, the software was made to classify the individual nanoparticles as primary or secondary particles (FIG. 15J) based on information the training database.

FIGS. 15A-J show an original image downloaded from TEM database (A); the image contrast enhancement by the algorithm of histogram equalization (B); back ground noise intensification due to the procedure of enhancing image contrast (C); reduction of background noise level by a moving average filter, while retaining the signal intensity of a particle (D); an original image downloaded from TEM database (E); isolation of signal of particle from the image by using interactive selection method (F); zoom in image of the original image (G); no obvious feature distortion (H) of isolated particles after image processing; a snapshot of the program which users used to build a training database by clicking individual particle (I) and (J). Primary particles are labeled in red dots (denoted "p" here), whereas the secondary particles are labeled with green dots (denoted "s" here) (I); The computer software enabled distinguishing of every particle (J).

FIG. 16A shows TEM image, size distribution and EDX analysis of ZnO nanoparticles in a sunscreen lotion. The sunscreen lotion was directly loaded into a specimen kit and dried for TEM observations. FIG. 16B shows TEM images, size distribution and EDX analysis of $TiO_2$ nanoparticles in a sunscreen lotion.

FIG. 17A shows TEM images of $CaCO_3$ particles in milk. The milk was directly loaded into the specimen kit and dried for TEM observations. FIG. 17B shows TEM images of primary and aggregated/agglomerated $CaCO_3$ particles in milk. FIG. 17C shows size distribution of summation, primary and aggregated/agglomerated $CaCO_3$ particles in milk. The milk was directly loaded into the specimen kit and dried for TEM observations.

The chamber's height in the TEM specimen kit described in FIGS. 16-17 was 2 μm. The sample such as lotion, milk, etc. was directly loaded into the specimen kit and dried for TEM observations.

FIG. 18A shows TEM images of abrasives in CMP slurry in aqueous environment observed by TEM/FEI/200 keV, TEM/Hitachi/100 keV, and STEM/FEI/30 keV. FIG. 18B shows TEM images and the size distribution of summation, primary and aggregated/agglomerated $SiO_2$ abrasives in CMP slurry. The CMP slurry in FIG. 18A-B was directly loaded into the TEM specimen kit with 0.2 μm chamber width and sealed by epoxy resin for TEM observations.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for preparing a specimen for TEM nanoparticle characterization, comprising:
 (a) providing a specimen kit comprising:
  (i) a top substrate and a bottom substrate, each of the substrates having a top surface and a bottom surface and a length of L1, a width of W1, and a thickness of T1, the top and the bottom substrates being transparent and substantially parallel to each other;
  (ii) a first spacer and a second spacer, each having a length of L2, a width of W2, and a thickness of h, located beneath the top substrate and sitting on the bottom substrate, the second spacer being positioned opposite to and spaced apart from the first spacer at a distance of d, wherein the width of the spacer W2 is smaller than the width of the top substrate W1; and
  (iii) a non-enclosed chamber having two ends open to the atmosphere and formed between the top and bottom substrates and between the first and second spacers, being characterized by having a length of L1, a width of d, and a height of h defined by the thickness of the spacer, wherein the height h being smaller than the diameter of a red blood cell;
 (b) loading a nanoparticle-containing liquid sample into the chamber; and
 (c) drying the liquid sample within the chamber to obtain a dry nanoparticle-containing specimen, wherein the nanoparticles are attached onto the bottom surface of the top substrate and the top surface of the bottom substrates.

2. The method of claim 1, wherein the nanoparticle-containing liquid sample is at least one selected from the group consisting of a blood sample, a bodily fluid, a lotion, a chemical mechanical polishing/planarization slurry, and a calcium carbonate nanoparticle-containing liquid or milk.

3. The method of claim 1, wherein during drying of the liquid sample the nanoparticles are restricted from movement and forming aggregation and/or agglomeration.

4. A method for analyzing TEM images of nanoparticles in a liquid sample, comprising:
 (a) preparing a dry specimen for TEM nanoparticle characterization according to the method of claim 1;
 (b) placing the dry specimen under a TEM; and
 (c) observing and analyzing the TEM images of nanoparticles in the dry specimen to obtain information on aggregation, agglomeration and/or concentration of the nanoparticles in the liquid sample.

5. The method of claim 4, wherein the observing and analyzing step further comprises:
 (i) acquiring TEM images of the nanoparticles and storing the TEM images in a computer;
 (ii) preprocessing the TEM images to enhance contrast, reduce noise and background;
 (iii) segmenting the nanoparticles in the images from the background;
 (iv) building a training database with a user interface; and
 (v) classifying individual nanoparticles based on information in the training database.

6. The method of claim 5, wherein steps (i)~(v) are performed with a computer software.

7. The method of claim 5, wherein the building step comprises training the computer to recognize properties of nanoparticles.

8. The method of claim 7, wherein the properties are at least one selected from the group consisting of aggregated particles and single particles.

9. A dry nanoparticle-containing specimen comprising:
 (a) nanoparticles in dry form evenly distributed within a non-enclosed chamber of a specimen kit, the distance between the nanoparticles exhibiting a uniform Gaussian distribution, wherein the specimen kit comprises:
  (i) a top substrate and a bottom substrate, each of the substrates having a top surface and a bottom surface, and a length of L1, a width of W1, and a thickness of T1, the top and the bottom substrates being transparent and substantially parallel to each other;
  (ii) a first spacer and a second spacer, each having a length of L2, a width of W2, and thickness of h, located beneath the top substrate and sitting on the bottom substrate, the second spacer being opposite to and spaced apart from the first spacer at a distance of d, wherein the width of the spacer W2 is smaller than the width of the top substrate W1; and
  (iii) a non-enclosed chamber having two ends open to the atmosphere and formed between the top and bottom substrate and between the first and second spacer, being characterized by having a length of L1, a width of d, and a height of h defined by the thickness of the spacer, wherein the height h being smaller than the diameter of a red blood cell; wherein the nanoparticles are loaded into the chamber as a non-dry particle form suspended in a liquid sample, and the nanoparticles in dry form evenly distributed within the chamber are attached onto the top surface of the bottom substrate and the bottom surface of the top substrate, and wherein the even distribution of the nanoparticles within the non-enclosed chamber reflects the status of the non-dry nanoparticles suspended in the liquid sample, and further wherein the dry specimen contains no cells.

10. A specimen kit comprising:
 (i) a top substrate and a bottom substrate, each of the substrates having a top surface and a bottom surface and a length of L1, a width of W1, and a thickness of T1, the top and the bottom substrates being transparent and substantially parallel to each other;
 (ii) a first spacer and a second spacer, each having a length of L2, a width of W2, and a thickness of h, located beneath the top substrate and sitting on the bottom substrate, the second spacer being positioned opposite to and spaced apart from the first spacer at a distance of d, wherein the width of the spacer W2 is smaller than the width of the top substrate W1; and
 (iii) a non-enclosed chamber having two ends open to the atmosphere and formed between the top and the bottom substrates and between the first and the second spacers, being characterized by having a length of L1, a width of d, and a height of h, defined by the thickness of the spacer, wherein the height h being smaller than the diameter of a red blood cell.

11. The specimen kit of claim 10, further comprising:
 (a) a top frame having a top surface and a bottom surface, the top frame being located on the top substrate and having an open window formed between the top surface and the bottom surface thereof; and
 (b) as bottom frame having a top surface and a bottom surface, the bottom frame being located beneath the bottom substrate and having an open window formed between the top surface and the bottom surface thereof;
 wherein each of the open windows has an window opening, facing the chamber and another window opening facing away from the chamber, the window opening facing the chamber has a width of no greater than 50 μm and a length of no greater than 800 μm.

12. The specimen kit of claim 10, wherein the top substrate further comprises a plurality of holes or channels or slits, the size of the holes or channels or slits being adapted to restrict the liquid sample within the chamber from slipping through the holes or channels or slits.

13. The specimen kit of claim 10, wherein the top and the bottom substrates each have a thickness ranging from 50 nm to 300 nm.

14. A system for analyzing TEM images of particles in a liquid sample, comprising:
 (a) the specimen kit of claim 10; and
 (b) a computer software containing algorithms to perform the following functions:
   (i) acquiring TEM images of nanoparticles and storing the images in a computer;
   (ii) pre-processing the TEM images to enhance contrast, reduce noise and background
   (iii) segmenting the nanoparticles in the images from the background;
   (iv) building a training database with a user interface; and
   (v) classifying individual particles based on information in the training database.

15. The system of claim 14, wherein the specimen kit further comprises:
 (a) a top frame having a top surface and a bottom surface, the top frame being located on the top substrate and having an open window formed between the top surface and the bottom surface thereof; and
 (b) a bottom frame having a top surface and a bottom surface, the bottom frame being located beneath the bottom substrate and having an open window formed between the top surface and the bottom surface thereof;
wherein each of the open windows has an window opening facing the chamber and another window opening facing away from the chamber, the window opening facing the chamber has a width of no greater than 50 μm and a length of no greater than 800 μm.

* * * * *